United States Patent [19]
McGuinness

[11] Patent Number: 5,624,387
[45] Date of Patent: Apr. 29, 1997

[54] CERVICAL BRACE

[76] Inventor: Charles McGuinness, 10 Karen Ave., Plainview, N.Y. 11803

[21] Appl. No.: 505,685

[22] Filed: Jul. 21, 1995

[51] Int. Cl.$^6$ ..................................................... A61F 5/00
[52] U.S. Cl. ............................................. 602/18; 602/17
[58] Field of Search .................................. 602/5, 17, 18, 602/19, 32–40; 128/DIG. 19, 23, 869

[56] References Cited

U.S. PATENT DOCUMENTS

| | | | |
|---|---|---|---|
| 2,474,200 | 6/1949 | McBee | 602/18 |
| 2,820,455 | 1/1958 | Hall | 602/18 |
| 2,904,040 | 9/1959 | Hale | 602/18 |
| 3,669,102 | 6/1972 | Harris | 602/40 |
| 4,541,421 | 9/1985 | Iversen | 602/18 |
| 4,951,655 | 8/1990 | MacMillan | 602/17 |
| 5,088,482 | 2/1992 | McGuinness | 602/32 X |
| 5,171,296 | 12/1992 | Herman | 602/5 |
| 5,195,947 | 3/1993 | Bode | 602/18 |
| 5,261,873 | 11/1993 | Bremer | 602/5 X |
| 5,385,535 | 1/1995 | McGuinness | 602/18 |

*Primary Examiner*—Linda C. Dvorak
*Attorney, Agent, or Firm*—Galgano & Burke

[57] ABSTRACT

A cervical brace includes a support brace which, in use, is receivable about and circumferentially surrounds a wearer's neck and is generally supportable on the wearer's shoulders and upper torso. The support brace includes a pair of spaced-apart generally vertically-extending, length-adjustable front struts, and a pair of spaced-apart, generally vertically extending, length adjustable rear struts, spaced rearwardly from the front struts, each of which struts has a top end and a bottom end, and two pairs of upper and lower spaced-apart, generally horizontally extending, length-adjustable side struts, each pair of which connects one of the front struts to the rear strut disposed rearwardly thereof. A pair of generally horizontally-disposed length adjustable front and rear cross braces connect the front and rear struts, respectively, together adjacent to lower ends thereof. A generally horizontally disposed, angle-, position- and length-adjustable chin support member assembly is mounted between the front struts adjacent to top ends thereof, and a generally-horizontally disposed and length adjustable head support assembly member is mounted between the rear struts adjacent to the top ends thereof for engaging and supporting the back of the head of the wearer.

13 Claims, 5 Drawing Sheets

CERVICAL BRACE

BACKGROUND OF THE INVENTION

The present invention relates to an improved cervical collar or brace. In general, cervical collars or braces are worn to correct or ease discomfort from spinal injuries, particularly spinal injuries in the area of the neck vertebrae. In particular, cervical braces are commonly used to rectify any spinal damage caused as a result of whiplash injury.

There are a number of types of such braces. For example, one type comprises a relatively stiff collar worn around the neck, which extends between the shoulders and the jawbone and chin of the wearer. While such collars do give a certain amount of support, they do not provide for adjustment to accommodate varying lengths of different people's necks. Thus, on some they may be relatively comfortable, while on others they can cause considerable discomfort. For example, in the case of an individual with a relatively short neck, such a collar may cause the chin to be retained at a totally incorrect angle. Further, for an individual with a relatively long neck, the chin may also be supported at the wrong angle. A further problem with such collars is that they are clearly visible for all to see and, in general, are relatively unsightly. Furthermore, because they are worn completely around the neck, there is very little circulation of air between the collar and the neck. Accordingly, they tend to induce perspiration in the neck area which further leads to discomfort.

Various attempts have been made to overcome the problems of such collars. Examples of such attempts are given in the following patent specifications, namely, U.S. Pat. Nos. 3,724,452, 3,945,376, 4,383,523 and 4,628,913, and UK Patent No. 2,233,900. In general, these cervical braces comprise a harness for mounting on the torso of the body, and a chin support member for supporting the chin of the wearer. The chin support member is mounted on a support bar which is adjustable upwardly and downwardly to accommodate wearers with different lengths of neck. However, while these devices partly overcome the problems of stiff collars in that at least the height at which the wearer's chin is supported can be adjusted, nonetheless they do not provide for the different positions which individuals chins may take up, in other words, the position of a wearer's chin front to back. Accordingly, while the chin supports may be adjusted to accommodate different heights of chins, this does not ensure that the chin support will accurately or correctly engage the wearer's chin. For example, if a wearer has a chin which projects more than normally, or a wearer has a chin which projects less than normally, then the chin support will not adequately support the wearer's chin.

Another known device is the "halo" brace. Such a device also has a harness for mounting on the torso and upright members which extend to the top of the wearer's head. A "halo" or ring is attached to the upright members which encircles the head in the forehead area. Four equally-spaced adjusting screws are installed in the halo and screwed toward the wearer's head. Depressions are made in the skull to receive the adjusting screws. The screws are tightened so as to restrict movement of the head and neck. However, the device is not very effective and, in addition, is bulky and unsightly. Furthermore, problems can develop with a single skull depression requiring total refitting of the device.

An improved cervical brace is described in my U.S. Pat. No. 4,793,334 (the subject matter of which is incorporated herein by reference thereto). This device overcame some of the problems with cervical braces, namely, the chin support member was adjustable both up and down, as well as front to back. However, the chin support member in this device was not comfortable as it "clamped" onto the wearer's chin. In addition, although a support is provided for the wearer's occiput, it is not sufficiently adjustable. Furthermore, the two-point support member for the chin support is not stable, i.e., it is flexible in the left-right direction. In addition, it has a complex harness assembly and requires changing the settings to remove the device.

In addition, a cervical collar is disclosed in *Arch Phys. Med. Rehabil.*, Vol. 73, December 1992, p. 573–575, made of rigid polythene, anatomically shaped with a cut out piece anterolaterally for ventilation. An anterior screw allows adjustment in length to variable neck height and the posterior Velcro® fastening allows adaptation to embrace all neck diameters. However, the device does not afford sufficient combinations of adjustability, rigidity (i.e., immobility) and ventilation for the purposes presently proposed.

In my prior patent, U.S. Pat. No. 5,088,482 (the subject matter of which is incorporated herein by reference thereto), a cervical brace is disclosed which utilizes the advantages found in my earlier U.S. Pat. No. 4,793,334, and overcomes the deficiencies in the aforementioned prior art. This patented cervical brace comprises a torso engaging member having a back portion and a front portion. The front portion in use being adjacent to the front of the torso and the rear portion, in use, being adjacent to the back of the torso. A chin support member is provided for engaging and supporting the chin of the wearer, together with mounting means including an adjustable and releasable strut and brace assembly for mounting the chin support member to the torso engaging member so that the chin support member is easily adjustable and is movable upwardly and downwardly in addition to backwardly and forwardly relative to the torso engaging member for accommodating, in use, different positions of a wearer's chin.

In my further prior patent, U.S. Pat. No. 5,385,535 (the subject matter of which is incorporated herein by reference thereto), a further improved cervical brace is disclosed which includes a generally annular support brace which, in use, is receivable about and circumferentially surrounds a wearer's neck and is generally supportable on the wearer's shoulders and upper torso. The support brace includes a pair of vertically-spaced-apart, interconnected and generally horizontally-disposed, arcuate, upper and lower support members each having a front central portion and a pair of rear opposite terminal end portions which, in use, are disposed generally adjacent to the front and rear of the wearer's neck, respectively, and adjustable and releasable rear strap means for joining said terminal end portions of said support members together. Chin support means are provided for engaging and supporting the chin of the wearer, as well as mounting means for adjustably mounting the chin support means on the support brace. This collar is extremely satisfactory in use and offers greater latitude in its adjustability to fit the particular wearer.

The present invention is directed toward an improvement of such cervical braces or collars.

SUMMARY OF THE INVENTION

Accordingly, it is an object of the present invention to provide an improved cervical brace which is universally and anatomically adjustable to accommodate a variety of users by providing height, width and depth adjustments in an easy and facile manner.

It is a further object of the present invention to provide such a brace which includes a chin support member for supporting a wearer's chin which can be adjusted to engage a patient's chin accurately and snugly, i.e., it is an object of the invention to provide a cervical brace in which the chin support member is adjustable in width upwardly and downwardly and also forwardly and rearwardly relative to the wearer.

It is also an object of the invention to provide an improved cervical brace which, as well as supporting the chin, also adjustably supports the back of the head of the wearer.

Another object of the invention is to provide a cervical brace which can be relatively easily fitted and removed.

It is a further object of the present invention to provide such a cervical brace which provides a more comfortable fit for the wearer while, at the same time, providing the degree of immobility required of the patient's neck.

Yet a further object is to provide a cervical brace with a plurality of adjustments that can easily be made by an individual with relatively little training with the device.

It is a more particular object of the invention to provide a cervical brace which provides support by non-intrusive means, i.e., fits externally on the wearer, is X-ray transmissive and provides essentially 360° of air ventilation around the wearer's neck.

Certain of the foregoing and related objects are readily attained in a cervical brace which includes a support brace which, in use, is receivable about and circumferentially surrounds a wearer's neck and is generally supportable on the wearer's shoulders and upper torso. The support brace includes a pair of spaced-apart generally vertically-extending, length-adjustable front struts, and a pair of spaced-apart, generally vertically extending, length adjustable rear struts, spaced rearwardly from the front struts, each of which struts has a top end and a bottom end, and two pairs of upper and lower spaced-apart, generally horizontally extending, length-adjustable side struts, each pair of which connects one of the front struts to the rear strut disposed rearwardly thereof. A pair of generally horizontally-disposed length adjustable front and rear cross braces connect the front and rear struts, respectively, together adjacent to lower ends thereof. A generally horizontally disposed angle-, position- and length-adjustable chin support member assembly is mounted between the front struts adjacent to top ends thereof, and a generally-horizontally disposed and length adjustable head support assembly member is mounted between the rear struts adjacent to the top ends thereof for engaging and supporting the back of the head of the wearer.

Preferably, the front side and rear struts each comprise turnbuckles for adjusting the length thereof. Most desirably, the front and rear cross braces are each comb-like having a multiplicity of spaced-apart slots and wherein the support arms each have a pin mounted thereon which is releasably engagable with one of the slots.

Advantageously, the collar additionally includes strap means releasably attachable to the support brace, which includes a pair of straps, each of which is receivable under an arm of the wearer for connecting the support brace to the wearer's torso. The collar also preferably includes a skull cap for mounting on the wearer's head which is releasably attachable to the support brace.

In a preferred embodiment of the invention, the head support member comprises a length-adjustable strut, the ends of which are each supported by strut support members which, in turn, adjustably support a head-engaging resilient member.

Most advantageously, the strut support members preferably each have a bore formed thereon and the head-engaging resilient members are each mounted on a pin frictionally receivable in the bore to allow for extension and retraction thereof, as well as adjustment of the rotational position thereof. Most desirably, the head-engaging resilient members each comprise a cup mounted in an off-center manner on the pins.

In a further embodiment of the invention, the chin support assembly comprises a length adjustable, generally horizontally disposed chin support bar and a pair of generally vertically-disposed lateral end plates, each joined to an opposite lateral end of the chin support bar. The lateral end plates are preferably mountable adjacent to the top ends of the opposite front struts in a pivot-, height- and depth-adjustable manner.

The lateral end plates are advantageously provided with a plurality of spaced-apart holes formed therethrough and the collar additionally includes a pair of upper support members each joining the top end of the front struts to a front end of the upper side struts via threaded throughbores formed therein and releasable locking means including a pair of threaded locking pins each of which is releasably received in one of the holes and throughbores so as to lock the lateral end plates and, in turn, the chin support bar, at a fixed axial pivot position angle with respect to the upper support members.

Most desirably, the support brace is made from X-ray transmissive material, such as plastic.

BRIEF DESCRIPTION OF THE DRAWINGS

Other objects and features of the present invention will become apparent from the following detailed description considered in connection with the accompanying drawings. It should be understood, however, that the drawings are designed for the purpose of illustration only and not as a definition of the limits of the invention.

In the drawings, wherein similar reference characters denote similar elements throughout the several views.

DETAILED DESCRIPTION OF THE PREFERRED EMBODIMENT

Figure 1:
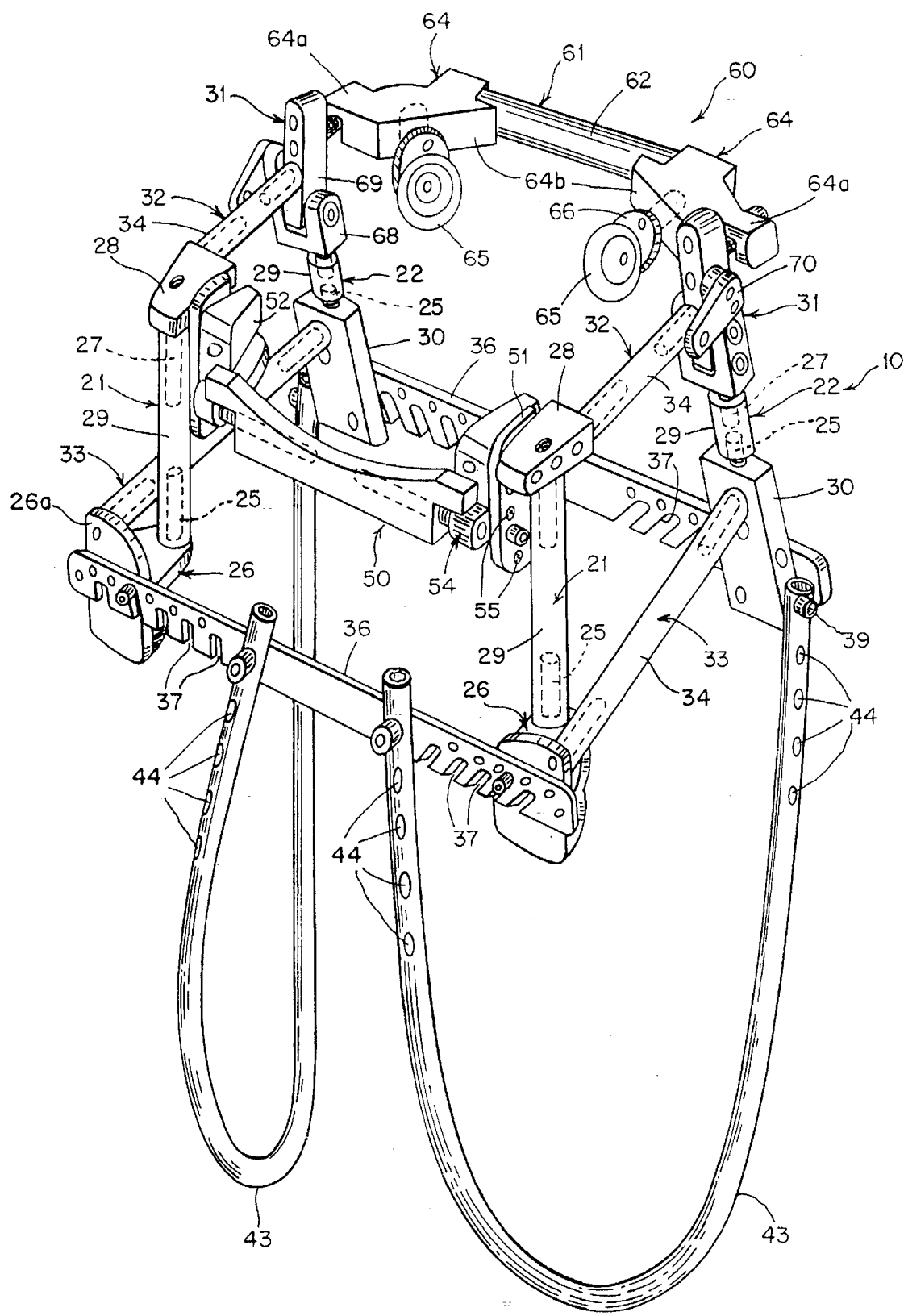
FIG. 1 is a front, top and left side perspective view of a cervical collar according to the invention.
Figure 2:
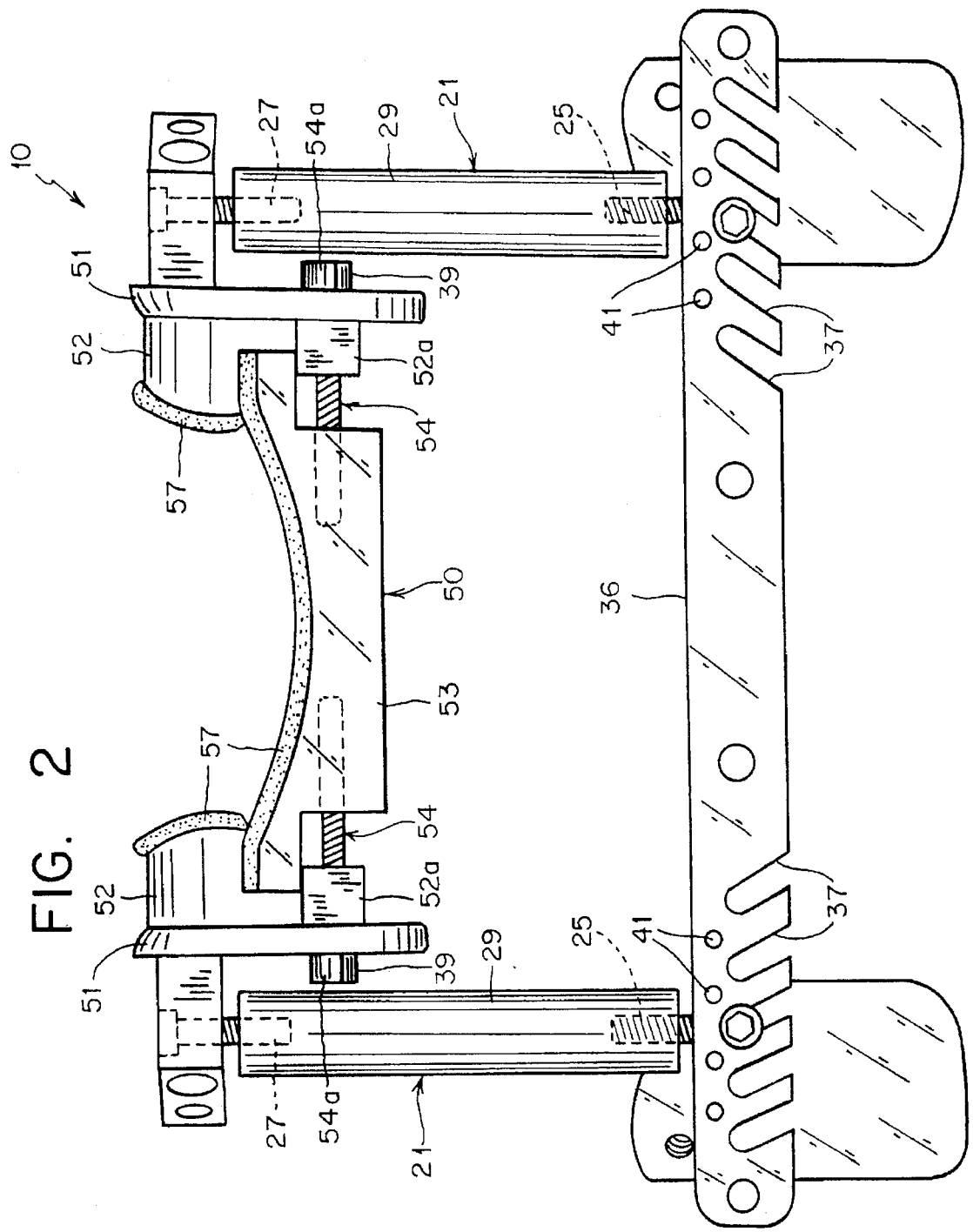
FIG. 2 is a front elevational view of the cervical collar.

Turning now in detail to the drawings, and in particular to FIGS. 1–4 thereof, therein illustrated is a cervical collar or support brace according to the invention, indicated generally by reference numeral 10. The cervical brace 10, in use, is receivable about and circumferentially surrounds a wearer's neck and is generally supportable on the wearer's shoulders and upper torso. The collar further includes a front chin support assembly 50 and a rear head support assembly 60 and is fully adjustable so that it can be accurately universally modified to fit the wearer's neck and head size (i.e., infant to adult).

The support brace 10 includes a pair of generally vertically extending, interconnected length adjustable front struts 21 (seen best in FIGS. 2 and 3) and a similar pair of rear struts 22 (seen best in FIGS. 3 and 4) preferably made of transparent or translucent plastic in the form of turnbuckles. The front turnbuckle struts 21 each comprise a lower left-handed, threaded rod 25 mounted on a generally L-shaped lower front support member or arm 26 and an upper right-handed, threaded member 27 mounted on upper front support member 28, on both of which is received an internally-threaded, cylindrical sleeve 29. The rear turnbuckle struts 22 are similarly designed and their lower rods 25 are mounted on lower rear support legs 30 and their upper rods 27 are mounted on upper rear support members 31.

The front and rear struts 21, 22 are joined by two pairs of upper and lower, spaced apart, generally horizontally extending length adjustable side struts 32, 33 also in the form of turnbuckles constructed in the same manner as front and rear struts 21, 22. The sleeves 34 of the upper side struts 32 are mounted via threaded rods 35 between upper front support member 28 and upper rear support member 31, and the sleeves 34 of lower side struts 33 are mounted via threaded rods 35 between the upper leg 26a of lower L-shaped front support 26 and lower rear support leg 30.

A generally horizontally disposed width or length adjustable front cross brace 36 joins the lower front support members 26 and a similarly designed rear cross brace 36 joins the two rear support legs 30. Cross braces 36 are comb-like and include a multiplicity of angled slots 37 opening onto a lower surface thereof which are receivable over the shaft 38 of a threaded pin 39 having an enlarged head 40. The threaded shafts 38 of each pin 39 is received in a threaded bore of each upper leg 26a of lower support member 26 and in each rear leg 30. The threaded pins 39 can be tightened to fix the effective length of braces 36 between struts 21 or struts 22 (depending on the slots 37 used). Alternatively, instead of slots 37, braces 36 are also provided with holes or bores 41 which can also be used for locking braces 36 to the support members 26, 30 via pins 39.

As a result of the foregoing construction, the height, width and depth of the collar can be adjusted as desired. Turning threaded, cylindrical sleeves 29 will either increase or decrease the effective length of the turnbuckle 21, 22 and, in turn, the overall height of the collar. Similarly, turnbuckles 32, 33 essentially control the spacing between the front and rear struts 21, 22 and, therefore, the "depth" of the collar. The "length" chosen for the cross braces 36, in cooperation with the "length" of the chin support assembly 50 and the rear head support assembly 60, will determine the effective "width" of the collar.

The cervical brace can be optionally affixed to the torso of the patient via straps 43 affixed to the rear legs 30, for example, via threaded pins 39 and threaded bores provided in the rear legs 30. The lower portion of the straps could be attached to a chest support assembly, such as that shown in U.S. Pat. No. 3,724,452, or they could be drawn underneath the patient's arms in a criss-cross fashion and back to the front of the collar, wherein they could be reattached via pins 39 to a threaded bore in cross brace 36. The straps 43 are preferably in the form of PVC tubing provided with a series of spaced apart adjustable holes 44 along their terminal ends. The base of lower front support member 26 is intended to rest forward of the wearer's clavicle, so as not to interfere with arm movement.

As shown best in FIGS. 1-4, the chin support assembly 50 is mounted generally between the upper support members 28 and includes a pair of generally vertically-extending lateral end plates 51, each of which is affixed via a threaded pin 39 to an opposite upper support member 28, and a pair of generally L-shaped lateral chin support plates 52, each of which are attached via threaded pins 39 to one of the lateral end plates 51. The L-shaped chin support plates 52 support the sides of the wearer's chin. They, in turn, support a length adjustable chin support bar 53 on which the base of the wearer's chin is supported. The ends of support bar 53 have threaded bores which receive threaded rods 54 which threadably extend through the lower leg 52a of chin support plates 52. By turning the heads 54a of threaded pins 54, one may laterally adjust the position of the chin rest, as well as fine tune its overall effective "width." By widening the chin rest, it allows the chin room to move forward or back and rest on the chin rest in the proper position prior to final adjustment. As can be appreciated, by narrowing the chin rest, a tighter fit is achieved between the chin support plates 52 and bar 53 so as to restrain the wearer's head wedged therebetween from moving from side to side, as well as forward to back.

Figure 3:
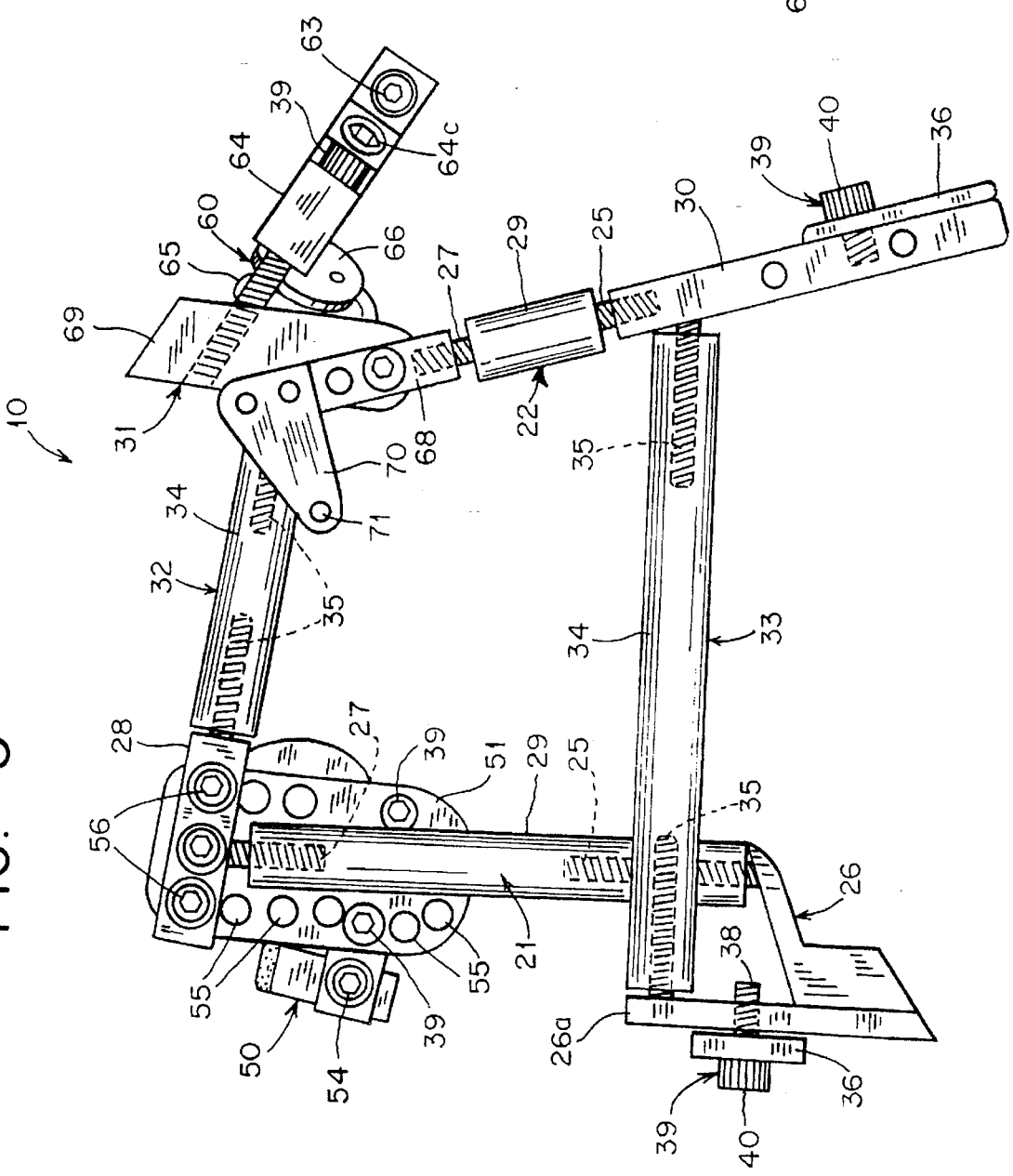
FIG. 3 is a side elevational view of the cervical collar.

As seen best in FIG. 3, the lateral end plates 51 have a series of spaced-apart adjustment holes 55 by which the doctor can adjust the pivot angle, height and depth of the chin support bar 53 relative to the upper support plate 28 via a pair of pins 39. The position Of the lateral end plates 51 is set by the provision of set screws 56 receivable through bores (not shown) provided in the support member 28 and, in turn, into one of the adjustment holes 55 of the lateral end plate 51. The lateral end plates 51 are joined to lateral chin support plates 52 via different threaded pins 39 so as to further increase the pivot and position adjustability of the chin support assembly 50 to accommodate the needs of the wearer.

Figure 6:
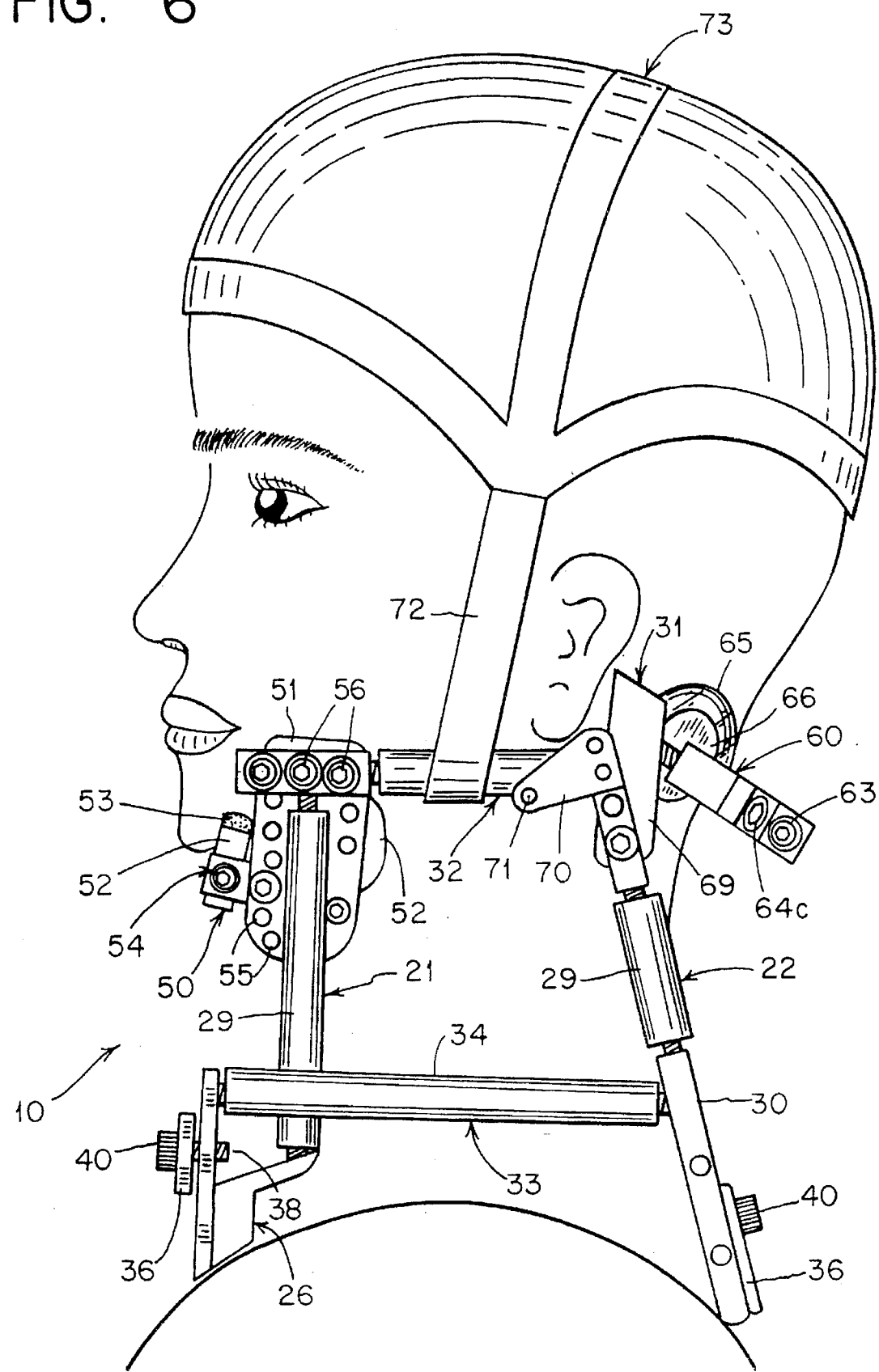
FIG. 6 is a side elevational view of the cervical collar showing the same being worn by a patient.

The chin support plate 53 and the lateral chin support plates 52 are provided with relatively soft, molded foam cushioning means, or chin support means 53, on which the chin of the wearer may also rest comfortably (see FIG. 6). As can be appreciated, the chin rest 57 can be modified to generally conform to the profile of the wearer's chin.

Figure 4:
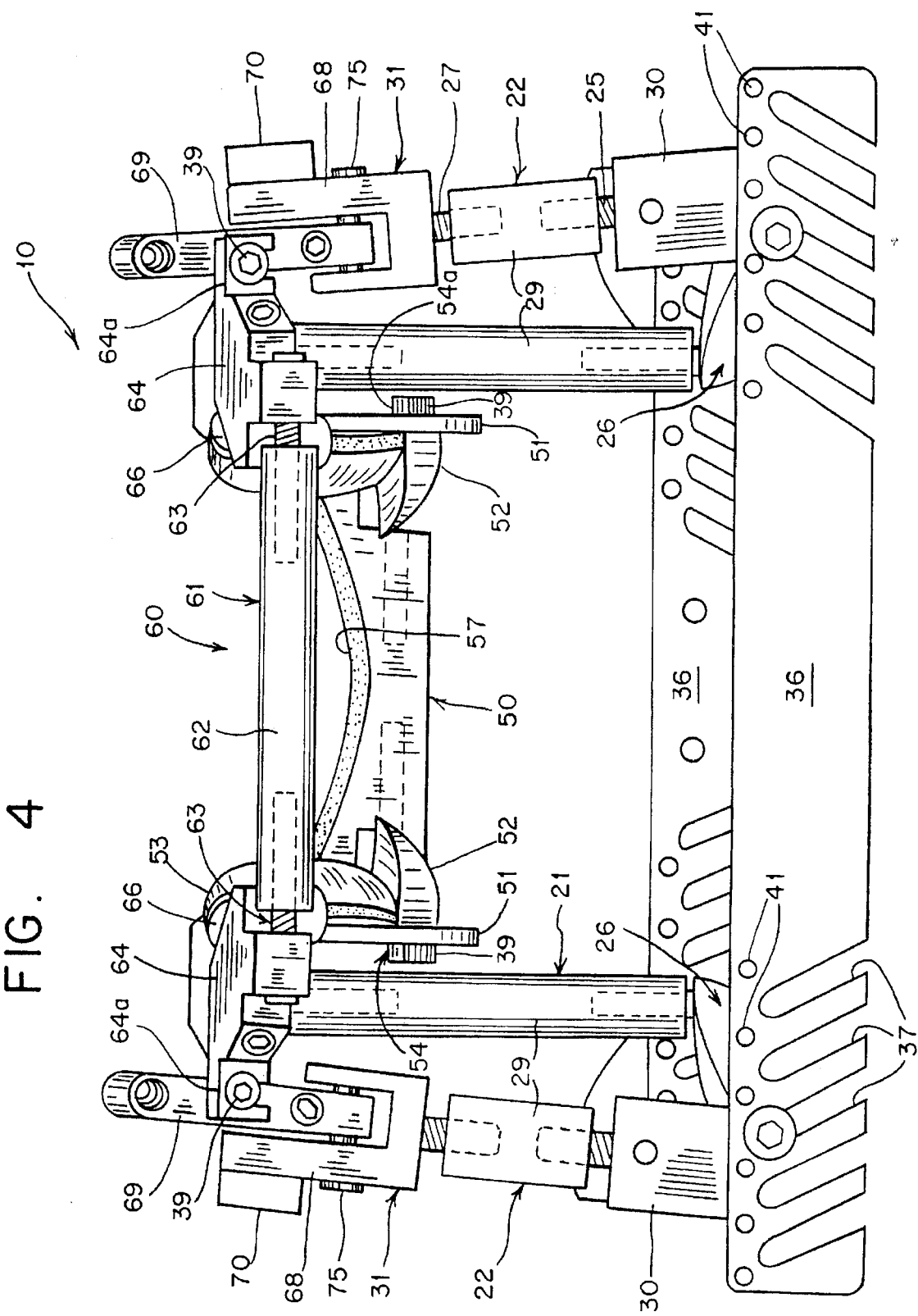
FIG. 4 is a rear elevational view of the cervical collar.

As seen best in FIGS. 1, 3, 4, the collar includes a rear head support assembly 60 generally supported between the upper rear support members 31. The head support assembly includes a horizontally-disposed, length-adjustable strut 61 composed of a cylindrical sleeve 62 having an internal threaded bore in opposite ends of which are received the ends of threaded rods or bolts 63, the opposite ends of which are received in said respective threaded bores of a generally L-shaped head support members 64. Head support members 64 have a notched first leg 64a by which it may be received on the shaft 38 of a threaded pin 39 received in the bore of the upper rear support member 31; the "notch" as opposed to a "bore" allows for easy and quick assembly and disassembly of the head support assembly. As can be appreciated, the effective length of strut 61 can be adjusted via rods 63 to accommodate the "width" adjustment of the collar as desired.

Head support members 64 each have a head-facing angled inner lateral wall 64b, from which inwardly projects a head-engaging, resilient plastic cup 65 which is intended to support the rear head portion of the wearer generally at a point adjacent to the base of the person's cranium. The cups 65 are each mounted on a circular disc 66 which, in turn, is mounted on a cylindrical shaft 67 connected thereto in an eccentric or axially offset manner. Shaft 67 is, in turn, frictionally received in a bore 64c (FIG. 3) provided in wall 64b.

Figure 5:
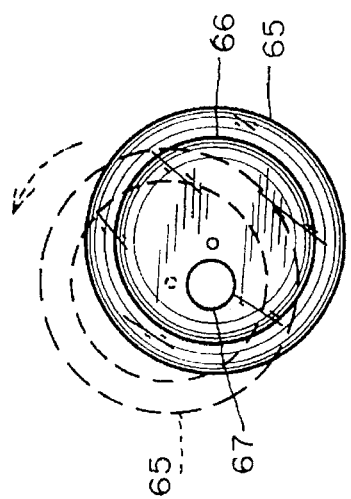
FIG. 5 is an enlarged, fragmentarily-illustrated plan view, in part section, of the collar's head support member, showing in phantom line various adjustable positions thereof.

As seen best in FIG. 5, the eccentric mounting of cups 65 allows the same to be rotated (via shaft 67) to a variety of positions, and in addition, it can be moved closer to or away from the wearer's head (via withdrawal or retraction of shaft 67) to accommodate the individual wearer's head; the cup assembly assuming its desired position due to the friction fit of the shaft and bore.

To further increase the adjustability of the head support assembly, the upper rear supports 31 preferably comprise a two-part pivot assembly composed of a J- or U-shaped yoke member 68, which via a threaded pin 75 supports the lower end of a generally upstanding arm 69 at a fixed angle pivot position, to which the head support assembly is mounted, as previously described. The fixed pivot angle arrangement allows the head support assembly to be aligned at an angle to the wearer's head, thereby providing a more comfortable and accommodating fit. Yoke member 68 additionally includes a triangular support 70 secured thereto having a hole or bore 71 by which a head or torso support strap can be secured.

As shown in FIG. 6 which illustrates the collar as it is intended to be worn by a patient, the collar optionally includes a releasable skull cap 73. Skull cap 73 has straps 72 which interconnects the skull cap to the upper side struts 32 preferably via VELCRO® loop and hook fasteners (not shown) provided on the ends thereof for effective releasible attachment thereof. The skull cap serves to restrain head movement. In place of the skull cap, the head support assembly disclosed in my earlier U.S. Pat. No. 5,385,535 could be employed.

Most desirably, the various components of the present cervical collar are fabricated from X-ray transmissive materials, such as plastic. It is also preferable that the plastic employed be transparent or translucent so that it will not be noticeable for aesthetic reasons.

As can be appreciated, the present invention provides a widely versatile cervical base which can be easily and universally adjusted to support the particular size and shape head of the wearer via its various adjustment features, which allow forward, rearward, upward, downward, lateral (widening or narrowing) and angular adjustment to accommodate differently dimensioned patients' heads and which affords a highly effective combination of rigidity and resiliency to provide a comfortable, yet medically proper, fit, which immobilizes the patient's head.

It should also be noted that the brace can be easily fitted onto the patients head from the front or either side, in the case of an emergency or accident when it is necessary to immobilize the patients head prior to moving him or her. The brace may also be suitable for use with other head or neck injuries, such as a broken jaw.

Accordingly, while only one embodiment of the present invention have been shown and described, it is to be understood that many changes and modifications may be made thereunto without departing from the spirit and scope of the invention.

What is claimed is:

1. A cervical brace comprising:

a support brace which, in use, is receivable about and circumferentially surrounds a wearer's neck and is generally supportable on the wearer's shoulders and upper torso, said support brace including a pair of spaced-apart generally vertically-extending, length-adjustable front struts, and a pair of spaced-apart, generally vertically extending, length-adjustable rear struts, spaced rearwardly from said front struts, each of which struts has a top end and a bottom end, and two pairs of upper and lower spaced-apart, generally horizontally extending, length-adjustable side struts, each pair of which connects one of said front struts to the rear strut disposed rearwardly thereof, a pair of generally horizontally-disposed front and rear cross braces having an adjustable effective length and connecting said front and rear struts, respectively, together adjacent to lower ends thereof, a generally horizontally disposed angle-, position- and length-adjustable chin support member assembly mounted between said front struts adjacent to top ends thereof, and a generally-horizontally disposed and length-adjustable head support assembly member mounted between said rear struts adjacent to said top ends thereof for engaging and supporting the back of the head of the wearer.

2. The brace of claim 1, wherein said front, side and rear struts each comprise turnbuckles for adjusting the length thereof.

3. The brace of claim 2, wherein said front and rear struts each include a support arm joined to the lower end thereof, for engaging a front and rear portion of the wearer's shoulders.

4. The brace of claim 3, wherein said front and rear cross braces are each comb-like having a multiplicity of spaced-apart slots and wherein said support arms each have a pin mounted thereon which is releasably engagable with one of said slots.

5. The brace of claim 1, additionally including strap means releasably attachable to said support brace including a pair of straps, each of which is receivable under an arm of the wearer for connecting said support brace to the wearer's torso.

6. The brace of claim 1, additionally including a skull cap releasably attachable to said support brace.

7. The brace of claim 1, wherein said head support assembly member comprises a length-adjustable strut, the ends of which are each supported by strut support members which, adjustably supports a head-engaging resilient member.

8. The brace of claim 7, wherein each of said strut support members has a bore formed thereon and said head-engaging resilient members are each mounted on a shaft frictionally receivable in said bore to allow for extension and retraction thereof, as well as adjustment of the rotational position thereof.

9. The brace of claim 8, wherein said head-engaging resilient members each comprise a cup mounted in an off-center manner on said shafts.

10. The brace of claim 1, wherein said chin support assembly comprises a length-adjustable, generally horizontally disposed chin support bar and a pair of generally vertically-disposed lateral end plates, each connected to an opposite lateral end of said chin support bar, said lateral end plates being mountable adjacent to said top ends of opposite front struts in a pivot-, height- and depth-adjustable manner.

11. The brace of claim 10, wherein said lateral end plates each has a plurality of spaced-apart holes formed therethrough and wherein said braces additionally includes a pair of upper support members each joining the top end of said front struts to an end of said upper side struts which has threaded throughbores formed therein and releasable locking means including a pair of threaded locking pins, each of which is releasably received in one of said holes and throughbores so as to lock said lateral end plates and, said chin support bar, at a fixed angle and height with respect to said upper support members.

12. The brace of claim 1, wherein said support brace is made from X-ray transmissive materials.

13. The brace of claim 1, wherein said support brace is made from plastic.

* * * * *